(12) United States Patent
David et al.

(10) Patent No.: US 6,749,813 B1
(45) Date of Patent: Jun. 15, 2004

(54) FLUID HANDLING DEVICES WITH DIAMOND-LIKE FILMS

(75) Inventors: Moses M. David, Woodbury, MN (US); Louis C. Haddad, Mendota Heights, MN (US); Nicholas A. Lee, Woodbury, MN (US); Brian J. Gates, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/519,448

(22) Filed: Mar. 5, 2000

(51) Int. Cl.$^7$ .................................................. B01L 3/00
(52) U.S. Cl. ..................... 422/102; 422/99; 428/216
(58) Field of Search ................... 422/99–104; 428/216; 436/165

(56) References Cited

U.S. PATENT DOCUMENTS

| 4,552,791 A | 11/1985 | Hahn |
| 4,661,409 A | 4/1987 | Kieser et al. |
| 4,663,183 A | 5/1987 | Ovshinsky et al. |
| 4,698,256 A | 10/1987 | Giglia et al. |
| 4,777,090 A | 10/1988 | Ovshinsky et al. |
| 4,783,361 A | 11/1988 | Ovshinsky et al. |
| 4,812,344 A | 3/1989 | Jaeger et al. |
| 4,877,677 A | 10/1989 | Hirochi et al. |
| 4,960,643 A | 10/1990 | Lemelson |
| 4,974,498 A | 12/1990 | Lemelson |
| 5,021,628 A | 6/1991 | Lemelson |
| 5,040,501 A | 8/1991 | Lemelson |
| 5,041,303 A | 8/1991 | Wertheimer et al. |
| 5,047,131 A | 9/1991 | Wolfe et al. |
| 5,096,352 A | 3/1992 | Lemelson |
| 5,132,587 A | 7/1992 | Lemelson |
| 5,135,808 A | 8/1992 | Kimock et al. |
| 5,190,807 A | 3/1993 | Kimock et al. |
| 5,206,083 A | 4/1993 | Raj et al. |
| 5,268,217 A | 12/1993 | Kimock et al. |
| 5,273,788 A | 12/1993 | Yu |
| 5,352,493 A | 10/1994 | Dorfman et al. |
| 5,366,556 A | 11/1994 | Prince et al. |
| 5,455,072 A | 10/1995 | Bension et al. |
| 5,466,431 A | 11/1995 | Dorfman et al. |
| 5,547,723 A | 8/1996 | Williams et al. |
| 5,618,619 A | 4/1997 | Petrmichl et al. |
| 5,637,469 A | 6/1997 | Wilding et al. |
| 5,679,413 A | 10/1997 | Petrmichl et al. |
| 5,718,976 A | 2/1998 | Dorfman et al. |
| 5,740,941 A | 4/1998 | Lemelson |
| 5,750,075 A | 5/1998 | Spike |
| 5,788,766 A | 8/1998 | Yamamoto et al. |
| 5,842,787 A | 12/1998 | Kopf-Sill et al. |
| 5,888,594 A | 3/1999 | David et al. |
| 5,938,679 A | 8/1999 | Freeman et al. |
| 6,015,597 A | 1/2000 | David |
| 6,083,313 A | 7/2000 | Venkatraman et al. |
| 6,228,471 B1 | 5/2001 | Neerinck et al. |

FOREIGN PATENT DOCUMENTS

| EP | 0 267 679 B1 | 5/1988 |
| EP | 0 278 480 B2 | 8/1988 |

(List continued on next page.)

OTHER PUBLICATIONS

Moses et al., Diamond–like film–encapsulated fibers enable long–length grating production, LIGHTWAVE Special reports Jul. 2000.*

(List continued on next page.)

*Primary Examiner*—Lyle A. Alexander
(74) *Attorney, Agent, or Firm*—Christopher D. Gram; Robert W. Sprague

(57) ABSTRACT

Fluid handling devices including a substrate with a diamond-like film. The devices include capillaries and microfluidic articles.

30 Claims, 6 Drawing Sheets

FOREIGN PATENT DOCUMENTS

| | | |
|---|---|---|
| EP | 0 280 215 B1 | 8/1988 |
| EP | 0 395 198 A2 A3 | 10/1990 |
| EP | 0 469 926 A1 | 2/1992 |
| EP | 0 598 361 A1 | 5/1994 |
| EP | 0 856 592 A1 | 8/1998 ........... C23C/14/00 |
| EP | 0 885 983 A | 12/1998 |
| EP | 0 963 455 B1 | 12/1999 |
| EP | 0 988 406 B1 | 3/2000 |
| JP | 0 211 4 650 | 4/1990 |
| JP | 0 511 0 163 | 4/1993 |
| WO | WO 92/06843 | 4/1992 |
| WO | WO 94/07613 | 4/1994 |
| WO | WO 94/21372 | 9/1994 |
| WO | WO 95/24275 | 9/1995 |
| WO | WO 96/05942 | 2/1996 |
| WO | WO 96/39943 | 12/1996 |
| WO | WO 96/40446 | 12/1996 ........... B05D/3/02 |
| WO | WO 97/13263 | 4/1997 |
| WO | WO 97/40207 | 10/1997 ........... C23C/16/30 |
| WO | WO 97/48836 | 12/1997 ........... C23C/16/26 |
| WO | WO 98/21626 | 5/1998 |
| WO | WO 98/33948 | 8/1998 |
| WO | WO 98/39481 | 9/1998 |
| WO | WO 98/59089 | 12/1998 |
| WO | WO 99/10560 | 3/1999 |
| WO | WO 99/29477 | 6/1999 ........... B26B/21/54 |
| WO | WO 99/38034 | 7/1999 |
| WO | WO 99/65542 | 12/1999 |
| WO | WO 99/65664 | 12/1999 |

OTHER PUBLICATIONS

The 2002 Photonics Circle of Excellence Award Winners, 3M Co. Film and Light Management and Optical Components Program.*

David et al., "Plasma Deposition and Etching of Diamond–Like Carbon Films", *AlChE Journal*, vol. 37, No. 3, pp. 367–376, Mar. 1991.

Bray et al., "New family of tailorable thin–film coatings", *Advanced Materials & Processes*, 146, No. 6, pp. 31–34, Dec. 1994.

C. F. M. Borges, "A Novel Technique for Diamond Film Deposition Using Surface Wave Discharges," *Diamond and Related Materials*, vol. 4, pp. 149–154 (1995).

IBM Technical Disclosure Bulletin, "Magnetostrictive Molecule Separator Chromatography," US, IBM Corp., New York, vol. 37, No. 8, pp. 527–528 (Aug. 1994).

Aebersold et al., "Covalent Attachment of Peptides for High Sensitivity Solid–Phase Sequence Analysis," *Anal. Biochem.*, 187:56–65 (1990).

Bacon, *Silica Optical Fibers Application Note: The Mechanical Strength of Silica Optical Fibers*, 3M Fiber Optics Laboratory, West Haven, CT, Title page, publication page, table of contents and pp. 1–9 (1995).

David et al., "Plasma Deposition and Etching of Diamond–Like Carbon Films," *AlChE J.*, 37(3):367–376 (1991).

Joos et al., "Covalent Attachment of Hybridizable Oligonucleotides to Glass Supports," *Anal. Biochem.*, 247:96–101 (1997).

Mort et al., eds., *Plasma Deposited Thin Films*, CRC Press, Boca Raton, FL, Title Page, publication page and table of contents only, 5 pages (1986).

Rao et al., "Solid Phase Synthesis of the 3'-Terminal Nonadecaribonucleoside Octadecaphosphate Sequence of Yeast Alanine Transfer Ribonucleic Acid," *Tetrahedron Lett.*, 28(41):4897–4900 (1987).

"Sun International Division, Comar Inc.," *Corporate Capabilities*, p. 110 Company description, markets served, major products and facilities (undated).

Sun International Division, Comar, Inc., "Plate+™ glass coated microplate," and "MicroMat™," advertisement, (1999).

Van Der Voort et al., "Silylation of the Silica Surface A Review," *J. Liq. Chrom. Rel. Technol.*, 19(17&18):2723–2752 (1996).

* cited by examiner

FLUID HANDLING DEVICES WITH DIAMOND-LIKE FILMS

FIELD OF THE INVENTION

This invention relates to fluid handling devices, such as microfluidic articles, including surfaces with diamond-like films thereon.

BACKGROUND

Silica capillaries are used extensively in electrophoresis, gas chromatography, electrochromatography, microbore liquid chromatography, and other chemical analytical techniques. Optical detection methods such as UV absorbance and fluorescence are often used in electrophoresis, electrochromatography, and liquid chromatography. The optical properties of silica are generally ideal for these detection methods; however, the use of pure uncoated silica capillaries is not possible because the lack of a protective coating causes the capillaries to be extremely fragile. As such, uncoated silica capillaries frequently will break under normal handling conditions.

Because of this, a protective coating must be put on the capillaries during fabrication. Conventionally, a polyimide coating is used. This coating has excellent thermal properties and gives the capillary excellent strength so that it can be easily handled; however, it is opaque and highly fluorescent and thus it is necessary to remove this coating from the portion of the capillary that is in an optical detector. Removal is somewhat difficult and it renders that portion of the capillary very delicate and easily broken.

There has also been a drive towards reducing the size of instrumentation used for analyzing and otherwise manipulating fluid samples such as biological fluid samples. The reduced size offers several advantages, including the ability to analyze very small samples, increased analytical speed, the ability to use reduced amounts of reagents, and reduced overall cost.

Various devices for microfluidic applications have been proposed. These devices typically include a glass or silicon substrate having a lithographically patterned and etched surface provided with one or more structures forming a microfluidic handling architecture. Plastic substrates such as polyimides, polyesters, and polycarbonates have been proposed as well; however, such plastic materials typically do not wet well and lack an electroosmotic flow necessary for the flow of liquid through the microchannels of the microfluidic handling architecture.

SUMMARY

The present invention provides capillaries and other fluid handling devices, such as microfluidic articles, that include diamond-like films, preferably optically transmissive and/or hydrophilic diamond-like films. The articles of the present invention provide several advantages. For example, in the case of capillaries, optically transmissive diamond-like films do not necessarily have to be removed for detection. Hydrophilic diamond-like films provide good wetting and flow characteristics. For certain embodiments, particularly for certain microfluidic articles, the use of attachment chemistries that are used in conventional glass systems provide advantage.

The present invention provides a fluid handling device that includes a substrate and a diamond-like film (preferably one that is optically transparent and/or hydrophilic) disposed on at least a portion of the substrate. "Disposed" as used herein, means that the film is directly in contact with the substrate, bound or otherwise, or the film is in contact with one or more intervening layers, bound or otherwise. Herein, a film, rather than a coating, is disposed on a substrate. "Coating" as used herein, generally refers to a material that is first applied to a solid substrate in a liquid state, then solidified by UV radiation (photopolymerizable), heat (thermoset), or by removing solvent molecules from the coating solution.

Preferably, the fluid handling device is a capillary having an internal surface (which is typically a fluid handling surface) and an external surface (which is typically a non-fluid handling surface), wherein at least a portion of at least one of the internal or external surfaces has an optically transmissive diamond-like film disposed thereon. Preferably, the external surface of the capillary has an optically transmissive diamond-like film disposed on at least a portion thereof.

In another preferred embodiment, the fluid handling device can be a microfluidic article having microfluidic handling architecture including a fluid handling surface with an optically transmissive and/or hydrophilic diamond-like film disposed on at least a portion thereof. "Microfluidic handling architecture" includes, without limitation, open and closed or covered microchannels, reservoirs, sample handling regions and combinations thereof. The architecture may also, or alternatively, include a non-fluid handling surface having an optically transmissive and/or hydrophilic diamond-like film disposed on at least a portion thereof. Preferably, at least a portion of the fluid handling surface includes a hydrophilic diamond-like film disposed thereon.

In a preferred embodiment, a microfluidic article includes a fast polymeric substrate having a first major surface that includes a plurality of microfluidic handling architectures and a second major surface, wherein the article is in the form of a roll.

In another embodiment, the present invention provides a fluid handling device that includes a substrate and an optically transmissive and/or hydrophilic film including at least about 25 atomic percent carbon, from 0 to about 50 atomic percent silicon, and from 0 to about 50 atomic percent oxygen, on a hydrogen-free basis, disposed on at least a portion of the substrate. "Hydrogen-free basis" refers to the atomic composition of a material as established by a method such as Electron Spectroscopy for Chemical Analysis (ESCA), which does not detect hydrogen even if large amounts are present in the thin films.

In yet another embodiment, the present invention provides a fluid handling device that includes a substrate and a film including at least about 30 atomic percent carbon, at least about 25 atomic percent silicon, and less than about 45 atomic percent oxygen, on a hydrogen-free basis, disposed on at least a portion of the substrate. Preferably, the film is optically transparent, and more preferably hydrophilic.

In still another embodiment, a fluid handling device is provided that includes a microfluidic article that includes a microfluidic handling architecture including a non-fluid handling surface wherein at least a portion thereof has disposed thereon a diamond-like film that is optically transmissive, hydrophilic, or both.

The present invention provides a method of manufacturing a hydrophilic diamond-like film. The method includes treating a diamond-like film in an oxygen-containing plasma Various other features and advantages of the present invention should become readily apparent with reference to the following detailed description, examples, claims and appended drawings.

Definitions

The present invention provides capillaries and microfluidic articles, as well as other fluid handling devices, and methods of manufacturing the same. For purposes of this invention, the following definitions shall have the meanings set forth.

"A" or "an" refers to one or more of the recited elements.

"Affix" shall include any mode of attaching reactants to a diamond-like film. Such modes shall include, without limitation, covalent and ionic bonding, adherence, such as with an adhesive, physical entrapment, and adsorption. This may or may not require the use of linking agents.

"Analyte" shall mean a molecule, compound, composition or complex, either naturally occurring or synthesized, to be detected or measured in or separated from a sample of interest. Analytes include, without limitation, proteins, peptides, fatty acids, nucleic acids, carbohydrates, hormones, steroids, lipids, vitamins, bacteria, viruses, pharmaceuticals, and metabolites.

"Diamond-like film" refers to substantially or completely amorphous films including carbon, and optionally including one or more additional components selected from the group of hydrogen, nitrogen, oxygen, fluorine, silicon, sulfur, titanium, and copper. Other elements may be present in certain embodiments. The films may be covalently bonded in a random system or in an interpenetrating system, such as in an interpenetrating diamond-like nanocomposite (called DYLYN), as described, e.g., U.S. Pat. No. 5,466,431. The amorphous diamond-like films of this invention may contain clustering of atoms that give it a short-range order but are essentially void of medium and long range ordering that lead to micro or macro crystallinity which can adversely scatter actinic radiation having wavelengths of from 180 nm to 800 nm. The term "amorphous" means a substantially randomly-ordered non-crystalline material having no x-ray diffraction peaks or modest x-ray diffraction peaks. When atomic clustering is present, it typically occurs over dimensions that are small compared to the wavelength of radiation.

"Hydrophilic" as it relates to a diamond-like film shall mean a diamond-like film having a water contact angle of about 50 degrees or less, and preferably about 30 degrees or less.

"Linking agent" shall mean any chemical species capable of affixing a "Reactant" to the diamond-like film. Linking agents can be covalently bonded to the diamond-like film or provided by a polymeric coating thereon.

"Optically transmissive" as it relates to a film refers to the film having an extinction coefficient of no greater than 0.3 at 500 nanometers (nm). Preferably, the extinction coefficient is no greater than 0.010 at 250 nm.

"Reactant" shall mean any chemical molecule, compound, composition or complex, either naturally occurring or synthesized, that is capable of binding an analyte in a sample of interest either alone or in conjunction with a molecule or compound that assists in binding the analyte to the diamond-like film, such as, for example, a coenzyme. The reactants of the present invention are useful for chemical or biochemical measurement, detection or separation. Accordingly, the term "Reactant" specifically excludes molecules, compounds, compositions or complexes, such as ink, that do not bind analytes as described above. Examples of reactants include, without limitation, polypeptides (e.g., proteins such as enzymes and antibodies), polynucleotides (e.g., oligonucleotides and cDNA), and carbohydrates.

BRIEF DESCRIPTION OF THE INVENTION

DETAILED DESCRIPTION OF THE PREFERRED EMBODIMENTS

The present invention provides capillaries and other fluid handling devices, such as microfluidic articles, having disposed on at least a portion thereof a diamond-like film, preferably one that is optically transmissive and/or hydrophilic. In the case of optically transmissive films, such films typically provide strength to the device, and preferably exhibit very low fluorescence. While providing strength, the films can also maintain a degree of flexibility. For fluid handling surfaces, hydrophilic diamond-like films can provide hydrophilic surfaces that enhance fluid transport. Furthermore, if desired, such films can include linking agents for affixing reactants or otherwise altering the surface chemistry. The films can also function as a barrier to liquid evaporation and transmission through the substrate of which the device is made.

Figure 1:
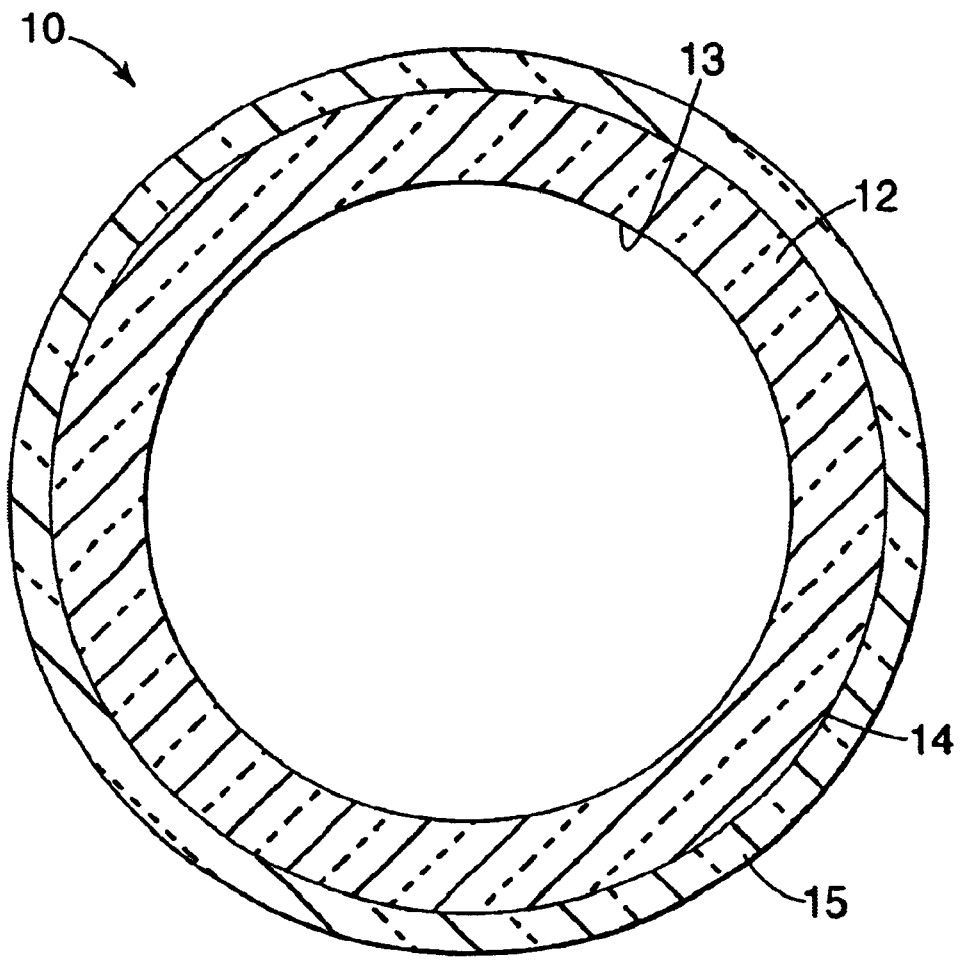
FIG. 1 is a cross-section of a capillary showing a diamond-like film on the external surface of the capillary.

Referring to FIG. 1, the present invention provides an exemplary capillary 10 that includes a substrate 12 with an internal surface 13 and an external surface 14, at least one of which has an optically transmissive diamond-like film 15 disposed thereon. The capillary can be made of glass or plastic. Typically, it is made of glass. According to the present invention, at least a portion of either the internal surface or the external surface, or both, has an optically transmissive diamond-like film thereon. Placing an optically transmissive diamond-like film on the external surface 14 of a glass capillary eliminates the need for a polymeric coating, such as polyimide, to provide strength. Placing a diamond-like film of the external surface 14 of a plastic capillary reduces or prevents evaporation and transmission of the liquid, e.g., water, through the plastic substrate. Placing a diamond-like film on the internal surface 13 of a glass or plastic capillary provides the capability of varying the surface chemistry, and preferably provides a hydrophilic surface if a hydrophilic diamond-like film is used.

Figure 2:
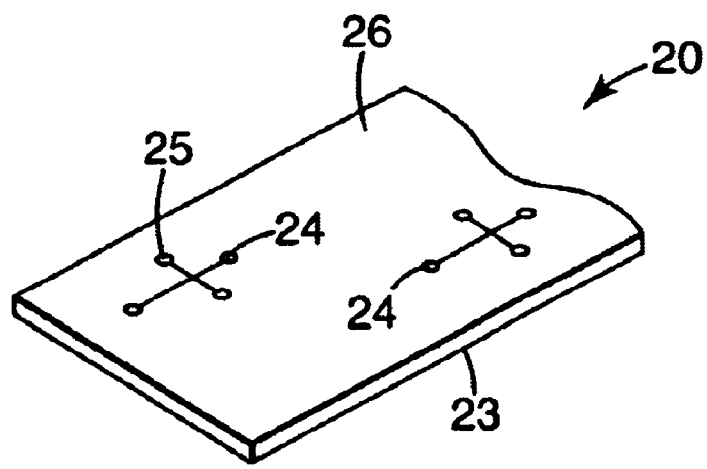
FIG. 2 is a perspective view of a microfluidic article showing a diamond-like film on a non-fluid handling surface of the article.

Referring to FIG. 2, an exemplary microfluidic device is shown that is a single layer article 20 in the form of a sheet featuring a polymeric substrate (e.g., plastic substrate) 23 bearing a plurality of microfluidic handling architectures 24.

The microfluidic handling architectures include a fluid handling surface 25. At least a portion of the fluid handling surface can include a diamond-like film that is either optically transmissive, hydrophilic, or both, disposed thereon, for similar reasons as described above for the capillaries. Significantly, for the fluid handling surfaces of such polymeric substrates, hydrophilic diamond-like films are preferred. Such hydrophilic diamond-like films, particularly, diamond-like glass films, can provide a surface that is more easily wettable and has a surface charge that allows electroosmotic flow that enhances fluid transport. With continuing reference to FIG. 2, the article may optionally include a non-fluid handling surface 26, at least a portion of which may include a diamond-like film disposed thereon.

Figure 3:
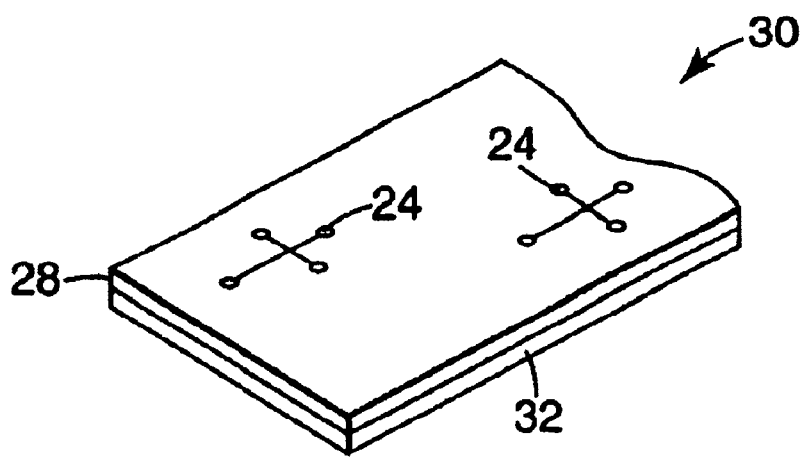
FIG. 3 is a perspective view of an alternative microfluidic article showing a diamond-like film on a fluid handling surface of the article.

Referring to FIG. 3, another exemplary embodiment of a microfluidic article 30 is shown that includes a first non-elastic (i.e., having insufficient elasticity in the direction normal to the plane of the substrate to act as a pump or valve when subjected to a cyclically varying force in that direction), polymeric substrate 28 having a first major surface that includes a microfluidic handling architecture 24, and a second major surface, and a second polymeric substrate 32 that is integrally bonded (i.e., bonded directly to each other, as opposed to being bonded through an intermediate material such as an adhesive) to the second major surface of the first substrate. The second substrate is capable of forming a free-standing substrate in the absence of the first substrate. It provides mechanical support for the first substrate and also provides a means for incorporating additional features into the article such as microelectronic, microoptical, and/or micromechanical elements, thereby providing design flexibility. At least a portion of at least one of a surface, preferably a fluid handling surface, of the microfluidic handling architectures 24 has a hydrophilic diamond-like film disposed thereon. Preferably, the hydrophilic diamond-like film is also optically transmissive. The article preferably includes a cover layer overlying the microfluidic handling architecture. The cover layer, which may be bonded to the first surface of the first substrate, preferably is a polymeric layer.

In preferred embodiments, the diamond-like film can include linking agents and reactants thereon, as described more fully below. The linking agents are selected based on the reactants to be affixed to the film and the application for which the fluid handling device will be used.

Capillaries

A capillary is typically constructed of material that is sturdy and durable so that it can maintain its physical integrity through repeated use under normal conditions. It is typically constructed of nonconductive material. This is important for capillary electrophoresis, for example, so that high voltages can be applied across the capillary without generating excessive heat. Inorganic materials such as quartz, glass, fused silica, and organic materials such as polytetrafluoroethylene, fluorinated ethylene/propylene polymers, polyfluoroethylene, aramide, nylon (i.e., polyamide), polyvinyl chloride, polyvinyl fluoride, polystyrene, polyethylene, and the like, can be advantageously used to make capillaries.

The internal diameter (i.e., bore size) of the capillaries extends to a wide range of capillary sizes. In general, capillaries can range preferably from about 5 micrometers to about 300 micrometers in internal diameter. The length of the capillary can range preferably from about 50 millimeters to about 30 meters.

The use of machined channels (e.g., capillary arrays) instead of individual capillary tubes are also known and are within the scope of fluid handling devices described herein. With conventional technology, however, multiple individual capillaries are still the more developed format. However, the films described herein can also be applied to such capillary arrays having machined channels.

Where excitation and/or detection are effected through the capillary wall, a particularly advantageous capillary is one that is constructed of transparent material. A transparent capillary that exhibits substantially no fluorescence, e.g., that exhibits fluorescence lower than background level, when exposed to the light used to irradiate a target species is especially useful in cases where excitation is effected through the capillary wall. Although such capillaries are known, the majority have a coating of an organic polymer (e.g., polyimide) that is opaque and highly fluorescent and thus must be removed from the portion of the capillary that is in an optical detector. Significantly, the optically transmissive diamond-like films of the present invention have substantially no fluorescence. Thus, these films need not necessarily be removed for optical detection of the samples contained in the capillaries.

Microfluidic Articles

Examples of microfluidic articles are described in Published International Patent Application Nos. WO 99/65542 and WO 99/65664, both published Dec. 23, 1999, and U.S. Pat. Nos. 5,637,469 to Wilding et al, and U.S. Pat. Nos. 5,842,787 to Kopf-Sill et al. Typically, microfluidic articles are polymer-based. Preferably, they can be produced efficiently in commercial-scale quantities, e.g., in the form of a roll good, and can be selectively tailored to perform a variety of functions, including analytical functions.

A preferred microfluidic article can be made by bringing a moldable material and the surface of an open molding tool (i.e., a molding tool that lacks a sealed cavity found in closed molds, of the type used in injection molding) into line contact (i.e., the point at which the tool contacts the moldable material as defined by a line that moves relative to both the tool and the moldable material) with each other to imprint, for example, a microfluidic processing architecture onto the moldable material, as described in Published International Patent Application No. WO 99/65664, published Dec. 23, 1999. The resulting molded article is then separated from the molding surface of the tool.

The moldable material can be an embossable polymeric substrate, a flowable resin composition, which can be cured upon exposure to thermal or actinic radiation prior to separating the molded article from the molding surface, or a molten thermoplastic composition which is cooled while in contact with the molding surface to solidify it.

Typically, a flowable resin composition is introduced onto a major surface of a polymeric substrate, and the substrate and molding tool are moved relative to each other to bring the tool and flowable resin composition into line contact with each other. The net result is a two-layer structure in which a microfluidic handling architecture-bearing layer is integrally bonded to the polymeric substrate.

Examples of suitable moldable materials include poly (methylmethacrylate) polycarbonates, polyesters, and polyimides. Examples of suitable photocurable resin compositions include alkyl acrylates and methacrylates (e.g., polymethyl methacrylate). Other ingredients which may be incorporated in the composition include photoinitiators, thixotropic agents, plasticizers, toughening agents, pigments, fillers, abrasive granules, stabilizers, light stabilizers, antioxidants, flow agents, bodying agents, flatting agents, colorants, binders, blowing agents, fungicides, bactericides, surfactants, glass and ceramic beads, and reinforcing materials such as woven and non-woven webs of organic and inorganic fibers.

A substrate may be bonded to the molded article to form a cover layer overlying the microfluidic handling architecture. Preferably, the substrate is a glass or polymeric substrate, although rigid cover layers such as glass cover layers may be used as well. Examples of suitable polymeric substrates include polycarbonate, polyester, poly (methylmethacrylate), polyethylene, and polypropylene. Bonding may be effected using an adhesive or by laminating or solvent welding the cover layer directly to the microfluidic handling architecture-bearing substrate. In addition, the cover layer may be part of the analytical instrumentation with which the article is designed to be used.

Significantly, diamond-like films described herein may be selectively patterned on portions of the microfluidic handling architectures, thereby forming discontinuous films. Deposition of diamond-like films may occur either in-line during manufacture or in a subsequent operation. The diamond-like films may perform a variety of functions. For example, the films may be used to increase the hydrophilicity of the microfluidic handling architecture. They may reduce or prevent evaporation of the sample liquid. The diamond-like films, particularly the hydrophilic diamond-like glass films, may also facilitate wetting of the surfaces and enhance flow of the samples through the channels of the microfluidic handling architecture. They may also facilitate wicking a sizing gel into the microchannels of an electrophoresis device.

Layers of other inorganic materials may be selectively deposited on portions of the microfluidic handling architectures, as well, for example, using vacuum sputtering, electron beam deposition, solution deposition; or chemical vapor deposition. Such materials can be used to perform some of the same functions as that of the diamond-like films, and those that are conductive may also be used to form electrodes or diaphragms for piezoelectric or peristaltic pumping.

It is also possible to selectively deposit materials, such as reactants onto various portions of the microfluidic handling architecture. Alternatively, these materials may be deposited in a pre-determined pattern on the surface of the cover layer designed to contact the microfluidic handling architecture.

A microfluidic article can optionally include one or more microelectronic, microoptical, and/or micromechanical elements as well. Examples of microelectronic elements include conductive traces, electrodes, electrode pads, microheating elements, electrostatically driven pumps and valves, microelectromechanical systems (MEMS), and the like. Examples of microoptical elements include optical waveguides, waveguide detectors, reflective elements (e.g., prisms), beam splitters, lens elements, solid state light sources and detectors, and the like. Examples of micromechanical elements include filters, valves, pumps, pneumatic and hydraulic routing, and the like. The microelements may be incorporated in the cover layer, either surface of the microfluidic handling architecture-bearing substrate, an additional polymeric substrate bonded to the microfluidic handling architecture-bearing substrate, or a combination thereof.

Such articles can include a number of different microfluidic handling architecture designs. Accordingly, they can be used to perform numerous functions, including, for example, capillary array electrophoresis, kinetic inhibition assays, competition immunoassays; enzyme assays, nucleic acid hybridization assays, cell sorting, combinatorial chemistry, and electrochromatography.

The depth of a microchannel can be varied while maintaining a constant microchannel width. The microchannels can be used to construct vertically tapered inlet and outlet diffusers for a piezoelectric valve-less diffuser micropump, or used to provide electrokinetic zone control or electrokinetic focusing. Similarly, the width of a high aspect ratio microchannel can be tapered at constant depth. The resulting structure is also useful for providing electrokinetic zone control.

It is also possible to taper both the depth and width of the microchannels to provide a constant cross-sectional area or, alternatively, a constant cross-sectional perimeter. As a consequence of the constant cross-sectional area or perimeter, the resulting structure enables achievement of a constant voltage gradient throughout the length of the channel for predominantly electrophoretic flow or electroosmotic flow, thereby providing optical confinement for single molecule detection without loss of resolving power. This structure is also useful for providing a transition between low aspect ratio and high aspect ratio structures (e.g., high aspect ratio injection tees, low aspect ratio probe capture zones, microwell reactors, or piezoelectric drive elements) without loss of in electrokinetic resolving power. It is also possible to prepare two intersecting microchannels having different depths. This feature, in turn, may be exploited to create a microfluidic switch in a hydrophobic substrate. Because of the depth difference, fluid in one arm of the relatively shallow microchannel will not cross the intersection unless a buffer is introduced into the relatively deeper mricrochannel to bridge the intersection. The variable depth feature is also useful for preparing post arrays for corralling probe capture beads in an immnunoassay or nucleic acid assay, while simultaneously permitting the reporter reagent and fluid sample to flow freely.

Diamond-Like Films

Various diamond-like films are suitable for the present invention. Films typically include plasma and/or vapor deposited materials containing silicon atoms, such as silicon oxide films, silicon nitride films, silicon oxynitride films, plasma polymerized polysiloxane films, hydrogenated and nonhydrogenated amorphous silicon-containing films, silicon-doped diamond-like carbon films, and the like. See, for example, Applicants' Assignee's copending applications U.S. Ser. No. 09/519,449, filed on even date herewith and U.S. Ser. No. 09/519,444, filed on even date herewith; and Plasma Deposited Thin Films, J. Mort & F. Jansen, Eds.; CRC Press, Boca Raton, Fla. (1986).

As the term is used herein, "diamond-like film" refers to substantially or completely amorphous films including carbon, and optionally including one or more additional components selected from the group of hydrogen, nitrogen, oxygen, fluorine, silicon, sulfur, titanium, and copper. Other elements may be present in certain embodiments.

As noted above and described below, the diamond-like films include approximately 25 to approximately 100 atomic percent carbon, with optional additional components making up the remainder (references to compositional percentages herein refer to atomic percents). The films may be covalently coupled or interpenetrating. The amorphous diamond-like films of this invention may contain clustering of atoms that give a short-range order but are essentially void of medium and long range ordering that lead to micro or macro crystallinity which can adversely scatter actinic radiation having wavelengths of from 180 nm to 800 nm.

Several special classes of covalently bonded diamond-like films are useful in this invention, as long as they are optically transmissive and/or hydrophilic. Diamond-like carbon (DLC) films, which include carbon and up to about 70% hydrogen, preferably about 10% to about 70%, typically are not optically transmissive, as defined herein.

Another class of suitable diamond-like films include diamond-like networks (DLN). In DLN, the amorphous carbon-based system is doped with other atoms in addition to hydrogen. These may include fluorine, nitrogen, oxygen, silicon, copper, iodine, boron, etc. DLN contains at least about 25% carbon. Typically the total concentration of these one or more additional elements is low (less than about 30%) in order to preserve the diamond-like nature of the films.

A particularly preferred class of diamond-like film materials is diamond-like glass (DLG), in which the amorphous carbon system includes a substantial quantity of silicon and oxygen, as in glass, yet still retains diamond-like properties. In these films, on a hydrogen-free basis, there is at least about 30% carbon, a substantial amount of silicon (at least about 25%) and not more than about 45% oxygen. The unique combination of a fairly high amount of silicon with a significant amount of oxygen and a substantial amount of carbon makes these films highly transparent and flexible (unlike glass). Furthermore, DLG films can be surface modified in oxygen-containing plasma to produce hydrophilic surfaces that remain stable over time. This is a preferred film for use in the fluid handling devices of the present invention.

Thin films made in accordance with the invention may have a variety of light transmissive properties. Thus, depending upon the composition, the thin films may have increased transmissive properties at various frequencies. In specific implementations the thin film is at least 50 percent transmissive to radiation at one or more wavelengths from about 180 to about 800 nanometers. In other advantageous implementations the DLG film is transmissive to greater than 70 percent (and more advantageously greater than 90 percent) of radiation at one or more wavelengths from about 180 to about 800 nanometers. High transmissivity is typically preferred because it allows thicker films to be produced without significant reduction in radiation intensity passing through the film.

In addition, a class of interpenetrating diamond-like films are useful in this invention. These diamond-like thin films are called DYLYN and are interpenetrating systems of two materials. These interpenetrating diamond-like thin films are disclosed in U.S. Pat. No. 5,466,431.

Diamond thin films having significantly different properties from the amorphous diamond-like film of the present invention due to the arrangement and intermolecular bonds of carbon atoms in the specific material, have previously been deposited on substrates. The type and amount of intermolecular bonds are determined by infrared (IR) and nuclear magnetic resonance (NMR) spectra. Carbon deposits contain substantially two types of carbon-carbon bonds: trigonal graphite bonds ($sp^2$) and tetrahedral diamond bonds ($sp^3$). Diamond is composed of virtually all tetrahedral bonds, while amorphous diamond-like films are composed of approximately 50% to approximately 90% tetrahedral bonds, and graphite is composed of virtually all trigonal bonds.

The crystallinity and the nature of the bonding of the carbonaceous film determines the physical and chemical properties of the deposit. Diamond is crystalline, whereas the amorphous diamond-like films of the invention are a non-crystalline, amorphous material, as determined by x-ray diffraction. Diamond is essentially pure carbon, whereas diamond-like films can contain a substantial amount of additional components (up to approximately 50 atomic percent for a single non-carbon component, and up to approximately 75 atomic percent for the combination of all additional non-carbon components). These atomic percents can be determined by combustion analysis.

Diamond has the highest packing density, or gram atom density (GAD), of any material at ambient pressure. Its GAD is 0.28 gram atoms/cc. Amorphous diamond-like films have a GAD ranging from about 0.20 to 0.28 gram atoms/cc. In contrast, graphite has a GAD of 0.18 gram atoms/cc. The high packing density of amorphous diamond-like films affords excellent resistance to diffusion of liquid or gaseous materials. Gram atom density is calculated from measurements of the weight and thickness of a material. "Gram to atom" refers to the atomic weight of a material expressed in grams.

Amorphous diamond-like films are diamond-like because, in addition to the foregoing physical properties that are similar to diamond, they have many of the desirable performance properties of diamond such as extreme hardness (1000 to 2000 kg/mm$^2$), high electrical resistivity ($10^9$ to $10^{13}$ ohm-cm), a low coefficient of friction (0.1), and optical transparency over a wide range of wavelengths (an extinction coefficient of less than 0.1 in the 400 to 800 nanometer range).

Diamond films, as opposed to diamond-like films, also have some properties, which in many applications make them less beneficial as a protective layer than amorphous diamond-like films. Diamond films have grain structures, as determined by electron microscopy. The grain boundaries are a path for chemical attack and degradation of the substrates, and also cause scattering of actinic radiation. Amorphous diamond-like films do not have a grain structure, as determined by electron microscopy, and are thus well suited to applications wherein actinic radiation will pass through the film.

The polycrystalline structure of diamond films causes light scattering from the grain boundaries. Surprisingly, diamond-like films in accordance with the invention allow for excellent light transmission. Additionally, the visible light transmission of a carbon-, or carbon- and hydrogen-, based film is further improved by incorporating silicon and oxygen atoms into the amorphous diamond-like structure during the deposition process. This is not possible for crystalline diamond thin films because additional components will disrupt its crystalline lattice structure.

In creating a diamond-like film, various additional components can be incorporated into the basic amorphous carbon or carbon and hydrogen structure. These additional components can be used to alter and enhance the properties that the diamond-like film imparts to the substrate. For example, it may be desirable to further enhance the barrier and surface properties.

The additional components may include one or more of hydrogen (if not already incorporated), nitrogen, oxygen, fluorine, silicon, sulfur, titanium, or copper. Other additional components may also work well. The addition of hydrogen promotes the formation of tetrahedral bonds. The addition of fluorine is particularly useful in enhancing barrier and surface properties of the diamond-like film, including the ability to be dispersed in an incompatible matrix. The addition of silicon and oxygen tends to improve the optical transparency and thermal stability of the diamond-like film. The addition of nitrogen may be used to enhance resistance to oxidation and to increase electrical conductivity. The addition of sulfur can enhance adhesion. The addition of titanium tends to enhance adhesion as well as diffusion and barrier properties.

Diamond-like films can be deposited in a variety of thicknesses, depending on the deposition conditions and starting materials. For example, they can be a thin as about 10 Angstroms or as thick as about 10 micrometers (i.e., microns), if desired. Preferably, they are about 200 Angstroms thick to about 1 micron thick. More preferably, they are about 500 Angstroms thick to about 1000 Angstroms thick.

Adhesion of the diamond-like film to the substrate may be improved, if desired, by any of the methods known to one skilled in the art. These methods typically include various pre-treatments such as corona or plasma treatment.

In certain embodiments, diamond-like films, particularly hydrophilic diamond-like films, can include linking agents, and optionally reactants, to modify the chemistry of the surface of the fluid handling devices. The linking agents may be substantially over the entire area of a surface of the substrate, such as the major surface, or in spots that may be in a regular or irregular pattern on such surface. If desired, more than one type of linking agent may be on the substrate.

Reactants can be disposed on the diamond-like films, optionally through linking agents, to create binding sites. As described more fully below, with respect to the methods of the present invention, any number of processes known in the art may be used to introduce the reactants. It is understood that the mode of affixation may vary in accordance with the reactant or reactants employed.

The type of reactant used in the present invention will vary according to the application and the analyte of interest. For example, when characterizing DNA, oligonucleotides are preferred. When conducting diagnostic tests to determine the presence of an antigen, antibodies are preferred. In other applications, enzymes may be preferred. Accordingly, suitable reactants include, without limitation, polypeptides (e.g., proteins such as enzymes and antibodies), polynucleotides (e.g., nucleic acids, oligonucleotides, cDNA), and carbohydrates. Preferred reactants include proteins, nucleic acids, and carbohydrates.

Method for Forming Diamond-Like Films

The diamond-like films are deposited by plasma deposition onto substrates from gases using the methods and apparatus disclosed in Applicants' Assignee's copending applications U.S. Ser. No. 09/519,449, filed on even date herewith and U.S. Ser. No. 09/519,447, filed on even date herewith.

A typical system includes electrodes one or both of which are powered by RF and a grounded reaction chamber. A substrate is placed proximate the electrode and an ion sheath is formed around the powered electrode to establish a large electric field across the ion sheath. Plasma is generated and sustained by means of a power supply (an RF generator operating at a frequency in the range of about 0.001 Hz to about 100 MHz). To obtain efficient power coupling (i.e., wherein the reflected power is a small fraction of the incident power), the impedance of the plasma load can be matched to the power supply by means of matching network that includes two variable capacitors and an inductor, which is available from RF Power Products, Kresson, N.J., as Model # AMN 3000.

Briefly, the grounded reaction chamber is partially evacuated, and radio frequency power is applied to one of two electrodes. A carbon-containing source is introduced between the electrodes to form a plasma that includes reactive species in proximity to the electrodes, and to also form an ion sheath proximate at least one electrode. The substrate is exposed to the reactive species within the ion sheath that is proximate an electrode to form a diamond-like thin film on the substrate. The conditions can result in a thin film that includes a diamond-like covalent system that includes, on a hydrogen-free basis, at least 30 atomic percent carbon, from 0 to 50 atomic percent silicon, and from 0 to 50 atomic percent oxygen.

Deposition occurs at reduced pressures (relative to atmospheric pressure) and in a controlled environment. A carbon-rich plasma is created in a reaction chamber by applying an electric field to a carbon-containing gas. Substrates on which films are to be deposited are usually held in a vessel or container in the reactor. Deposition of the diamond-like film typically occurs at rates ranging from about 1 nanometer per second (nm/second) to about 100 nm/second (about 10 Angstrom per second to about 1000 Angstroms per second), depending on conditions including pressure, power, concentration of gas, types of gases, relative size of electrodes, etc. In general, deposition rates increase with increasing power, pressure, and concentration of gas, but the rates will approach an upper limit.

Species within the plasma react on the substrate surface to form covalent bonds, resulting in an amorphous diamond-like film on the surface of the substrates. A multiplicity of substrates may simultaneously have a film deposited on them during the process of this invention. The substrates can be held in a vessel or container within an evacuable chamber that is capable of maintaining conditions that produce diamond-like film deposition. That is, the chamber provides an environment that allows for the control of, among other things, pressure, the flow of various inert and reactive gases, voltage supplied to the powered electrode, strength of the electric field across the ion sheath, formation of a plasma containing reactive species, intensity of ion bombardment and rate of deposition of a diamond-like film from the reactive species.

Prior to the deposition process, the chamber is evacuated to the extent necessary to remove air and any impurities. Inert gases (such as argon) may be admitted into the chamber to alter pressure. Once the substrate is placed in the chamber and it is evacuated, a substance containing carbon (and usually hydrogen), and optionally a substance from which an additional component can be deposited, is admitted into the chamber and, upon application of an electric field, forms a plasma from which the amorphous diamond-like film is deposited. At the pressures and temperatures of diamond-like film deposition (typically, about 0.13 Pascals (Pa) to about 133 Pa (0.001 to 1.0 Torr) (all pressures stated herein are gauge pressure) and less than 50° C.), the carbon-containing substances and substances from which an optional additional component may be obtained will be in their vapor form.

For the deposition of carbon and hydrogen in a diamond-like film, hydrocarbons are particularly preferred, including acetylene, methane, to butadiene, benzene, methylcyclopentadiene, pentadiene, styrene, naphthalene, and azulene. Mixtures of these hydrocarbons may also be used. Gases containing optional additional components can also be introduced into the reaction chamber. Gases with low ionization potentials, i.e., 10 eV or less, typically are used for efficient deposition of the diamond-like film.

The additional optional diamond-like film components, including one or more of hydrogen, nitrogen, oxygen, fluorine, silicon, sulfur, titanium, or copper, may be introduced in vapor form into the reaction chamber during the deposition process. Typically, even when the sources for the additional components are solids or fluids, the reduced pressure in the deposition chamber added to the chamber while a carbon- or hydrocarbon-containing gas is sustaining the plasma and/or may be added to the chamber after the flow of carbon or hydrocarbon-containing gas has been stopped.

Sources of hydrogen include hydrocarbon gases and molecular hydrogen ($H_2$). Sources of fluorine include compounds such as carbon tetrafluoride ($CF_4$), sulfur hexafluoride ($SF_6$), perfluorobutane ($C_4F_{10}$), $C_2F_6$, and $C_3F_8$. Sources of silicon include silanes such as $SiH_4$, $Si_2H_6$, tetramethylsilane, and hexamethyldisiloxane. Sources of oxygen include oxygen gas ($O_2$), hydrogen peroxide ($H_2O_2$), water ($H_2O$), and ozone ($O_3$). Sources of nitrogen include nitrogen gas ($N_2$), ammonia ($NH_3$), and hydrazine ($N_2H_6$). Sources of sulfur include sulfur hexafluoride ($SF_6$), sulfur dioxide ($SO_2$), and hydrogen sulfide ($H_2S$). Sources of copper include copper acetylacetonate. Sources of titanium include titanium halides such as titanium tetrachloride.

The electrodes may be the same size or different sizes. If the electrodes are different sizes, the smaller electrode will have a larger ion sheath (regardless of whether it is the grounded or powered electrode). This type of configuration is referred to as an "asymmetric" parallel plate reactor. An asymmetric configuration produces a higher voltage potential across the ion sheath surrounding the smaller electrode. Establishing a large ion sheath on one of the electrodes is preferred for this invention because the substrate is preferably located within an ion sheath to benefit from the ion bombardment effects that occur within the sheath.

Preferred electrode surface area ratios are from 2:1 to 4:1, and more preferably from 3:1 to 4:1. The ion sheath on the smaller electrode will increase as the ratio increases, but beyond a ratio of 4:1 little additional benefit is achieved. The reaction chamber itself can act as an electrode. A preferred configuration for this invention includes a powered electrode within a grounded reaction chamber that has two to three times the surface area of the powered electrode.

In an RF-generated plasma, energy is coupled into the plasma through electrons. The plasma acts as the charge carrier between the electrodes. The plasma can fill the entire reaction chamber and is typically visible as a colored cloud. The ion sheath appears as a darker area around one or both electrodes. In a parallel plate reactor using RF energy, the applied frequency is preferably in the range of about 0.001 Megaherz (MHz) to about 100 MHz, preferably about 13.56 MHz or any whole number multiple thereof. This RF power creates a plasma from the gas (or gases) within the chamber. The RF power source can be an RF generator such as a 13.56 MHz oscillator connected to the powered electrode via a network that acts to match the impedance of the power supply with that of the transmission line and plasma load (which is usually about 50 ohms so as to effectively couple the RF power). Hence this is referred to as a matching network.

The ion sheath around the electrodes causes negative self-biasing of the electrodes relative to the plasma. In an asymmetric configuration, the negative self-bias voltage is negligible on the larger electrode and the negative bias on the smaller electrode is typically in the range of 100 to 2000 volts. While the acceptable frequency range from the RF power source may be high enough to form a large negative direct current (DC) self bias on the smaller electrode, it should not be high enough to create standing waves in the resulting plasma, which is inefficient for the deposition of a diamond-like film.

For planar substrates, deposition of diamond-like films can be achieved in a parallel plate reactor by placing the substrates in direct contact with a powered electrode, which is made smaller than the grounded electrode. This allows the substrate to act as an electrode due to capacitive coupling between the powered electrode and the substrate. This is described in M. M. David et al., *AIChE Journal*, 37, No. 3, p. 367 (1991). In the case of an elongate substrate, the substrate is optionally pulled through the vacuum chamber continuously while a continuous RF field is placed on the electrode and sufficient carbon-containing gas is present within the chamber. A vacuum is maintained at the inlet and exit of the chamber. The result is a continuous carbon-rich film on an elongated substrate, and substantially only on the substrate.

Methods of Optional Functionalization

The diamond-like film need not be functionalized in order to affix reactants thereto. However, depending on the mode of affixation, it may be desirable to functionalize the silicon-containing layer to create linking agents.

The type of functionalization will depend on the type of reactant(s). Preferably, a variety of conventional approaches to rendering the surfaces of silica (e.g., glass) materials chemically reactive are known and may be employed in the present invention to the extent their use creates linking agents on the substrate for subsequent affixation of reactants. These include using silane coupling agents such as amino silanes to provide amino functionality, carboxy silanes to provide carboxy functionality, epoxy silanes to provide epoxy functionality, mercapto silanes (e.g., those of the formula HS-L-Si(X)(Y)(Z) wherein L is divalent organic linking group, X is a hydrolyzable group such as alkoxy, acyloxy, amine or chlorine, Y and Z are hydrolyzable or nonhydrolyzable groups) to provide mercapto functionality, hydroxy silanes, such as glycidoxypropyl silanes, to provide hydroxy functionality, and the like. Conditions of such silylation reactions (i.e., silanization reactions) are generally known to one of skill in the art. Examples of other silylation reactions are described in Van Der Voort et al., *J. Liq. Chrom. & Rel Rechnol.*, 12, 2723–2752 (1996); Sudhakar Rao et al., *Tet. Lett.*, 28, 4897–4900 (1987); Joos et al., *Anal. Biochem.*, 247, 96–101 (1997); Aebersold et al., *Anal. Biochem.*, 187, 56–65 (1990); and International Publication No. WO 98/39481, published Sep. 11, 1998.

Reactants are introduced preferably for affixation to the linking agents to create binding sites. The modes of affixation may include, without limitation, physical means, such as for example, physically entrapping the reactants within the diamond-like film. In a preferred embodiment of the present invention, reactants are introduced to be affixed to the diamond-like film using linking agents affixed to the diamond-like film.

The devices of the present invention, preferably with affixed reactants, may be used for the separation, detection, and measurement of the species present in samples of biological, ecological, or chemical interest. Of particular interest are macromolecules such as proteins, peptides, saccharides and polysaccharides, genetic materials such as nucleic acids, carbohydrates, cellular materials such as bacteria, viruses, organelles, cell fragments, metabolites, drugs, and the like, and combinations thereof. Of particular interest are the group of macromolecules that are associated with the genetic materials of living organisms. These include nucleic acids and oligonucleotides such as RNA, DNA, their fragments and combinations, chromosomes, genes, as well as fragments and combinations thereof.

EXAMPLES

The following examples have been selected merely to further illustrate features, advantages, and other details of the invention. It is to be expressly understood, however, that while the examples serve this purpose, the particular ingredients and amounts used as well as other conditions and details are not to be construed in a matter that would unduly limit the scope of this invention.

Plasma Reactor Descriptions

Figure 4:
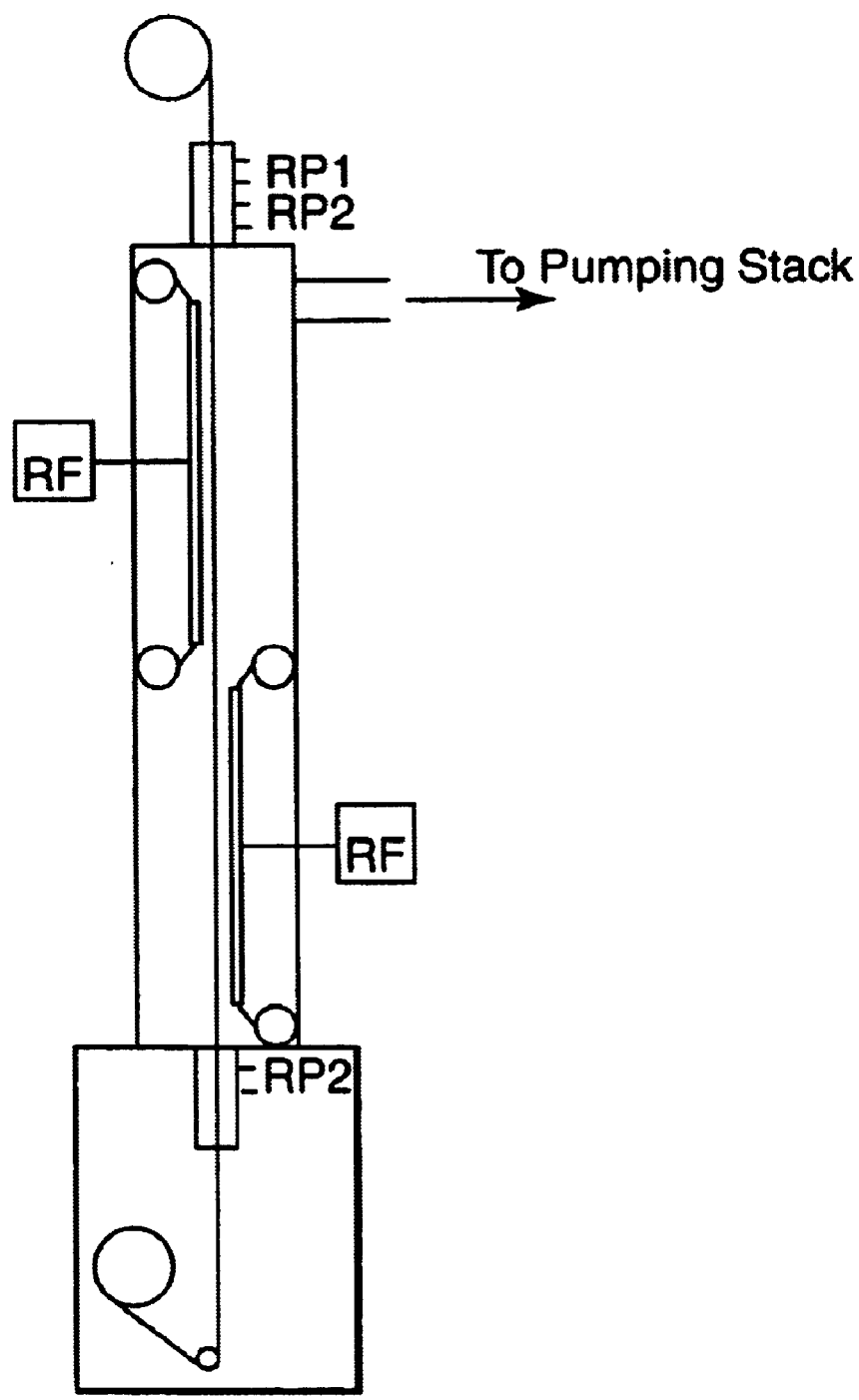
FIG. 4 is a schematic plan view of a plasma reactor used to prepare samples as further described in the Examples.

Reactor One: Diamond-Like Glass (DLG) films were deposited in a home-built plasma reactor designed specifically to deposit on fibers as depicted in FIG. 4. The reactor includes a vertical aluminum chamber having two linear aluminum electrodes that are nominally 610 mm (24 inches) long and 38 mm (1.5 inches) wide, located along the linear axis of the chamber, one above the other in a staggered arrangement. The sides and backside of the electrode are insulated and capped off with a ground plane so that only the front side of to the electrode is actively exposed to the plasma The electrodes are powered by a 1.0 kW RF power supply that was operated at a frequency of 13.56 MHz (Model RF 10S form RF Power Products, Kresson, N.J.) and matching network (Model CPM-1000 from Comdel Inc., Beverly, Mass. and controller (Model MatchPro CPM from Comdel Inc.). The feed gas or mixture of gases was introduced into the deposition chamber through mass flow controllers (from MKS Instruments, Andover, Mass.) and was pumped by a roots, blower (Model EH1200 from Edwards High Vacuum, Sussex, England) backed by a mechanical pump (Model E2M80 from Edwards High Vacuum). Pressure in the chamber was measured by a capacitance manometer and controlled by a throttle valve and controller (Models 653 and 600 series, respectively, from MKS instruments).

Figure 5:
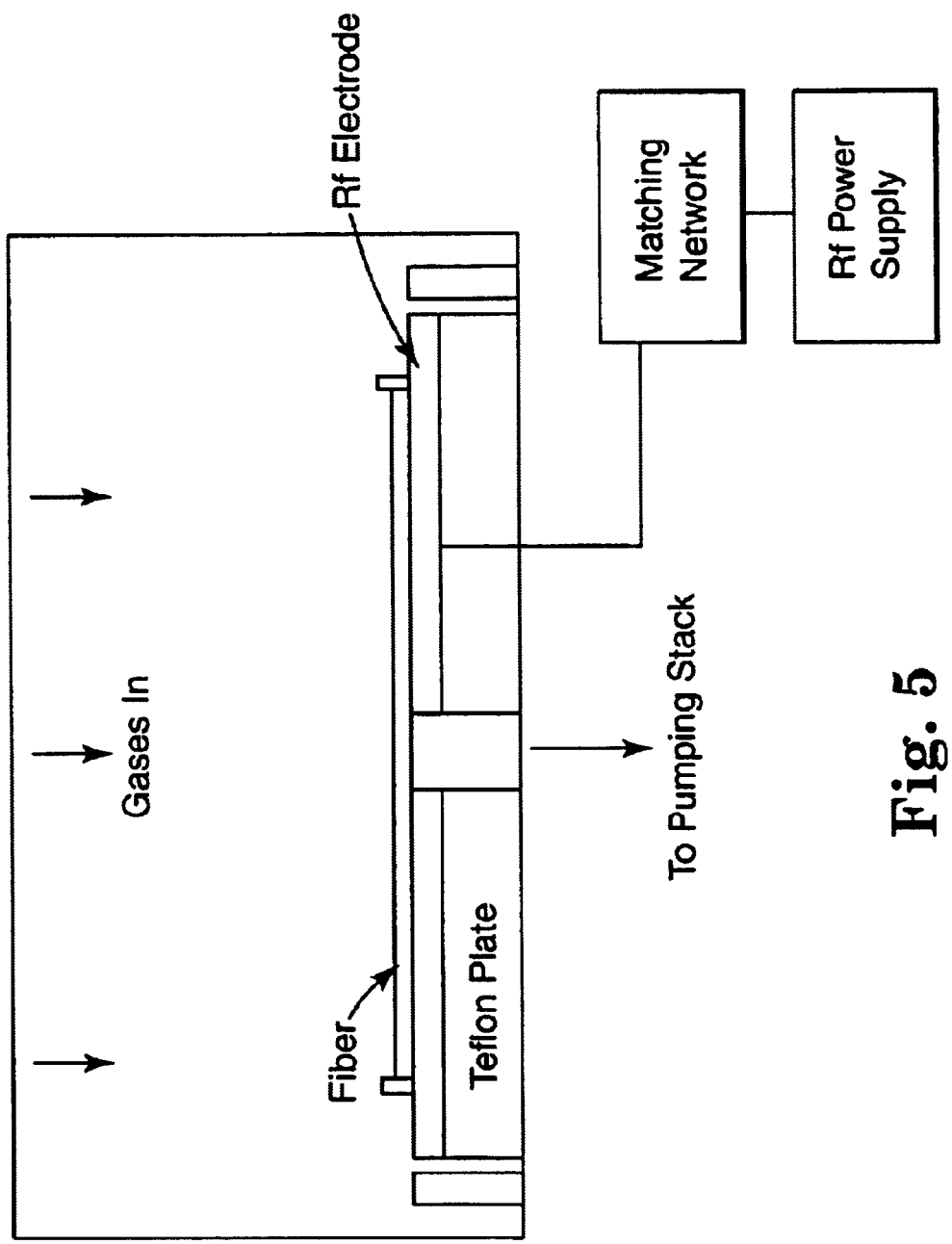
FIG. 5 is a schematic plan view of a plasma reactor used to prepare samples as further described in the Examples.

Reactor Two: A commercial parallel-plate capacitively coupled plasma reactor (commercially available as Model 2480 from PlasmaTherm of St. Petersburg, Fla.) was modified and used for the deposition of DLG onto capillary tubes. The reactor is depicted in FIG. 5. This reactor includes a grounded chamber electrode containing a powered electrode. The chamber is cylindrical in shape with an internal diameter of 26 inches and height of 12 inches. A circular electrode having a diameter of 55.9 cm (22 inches) was mounted inside and attached to a matching network and a 3 kW RF power supply that was operated at a frequency of 13.56 MHz. The chamber was pumped by a roots blower backed by a mechanical pump. Unless otherwise stated, the base pressure in the chamber was 0.67 Pa (5 mTorr). Process gases were metered into the chamber either through a mass flow controllers or a needle valve. All the plasma depositions and treatments were done with the substrate located on the powered electrode of the plasma reactor.

Example 1

Figure 6:
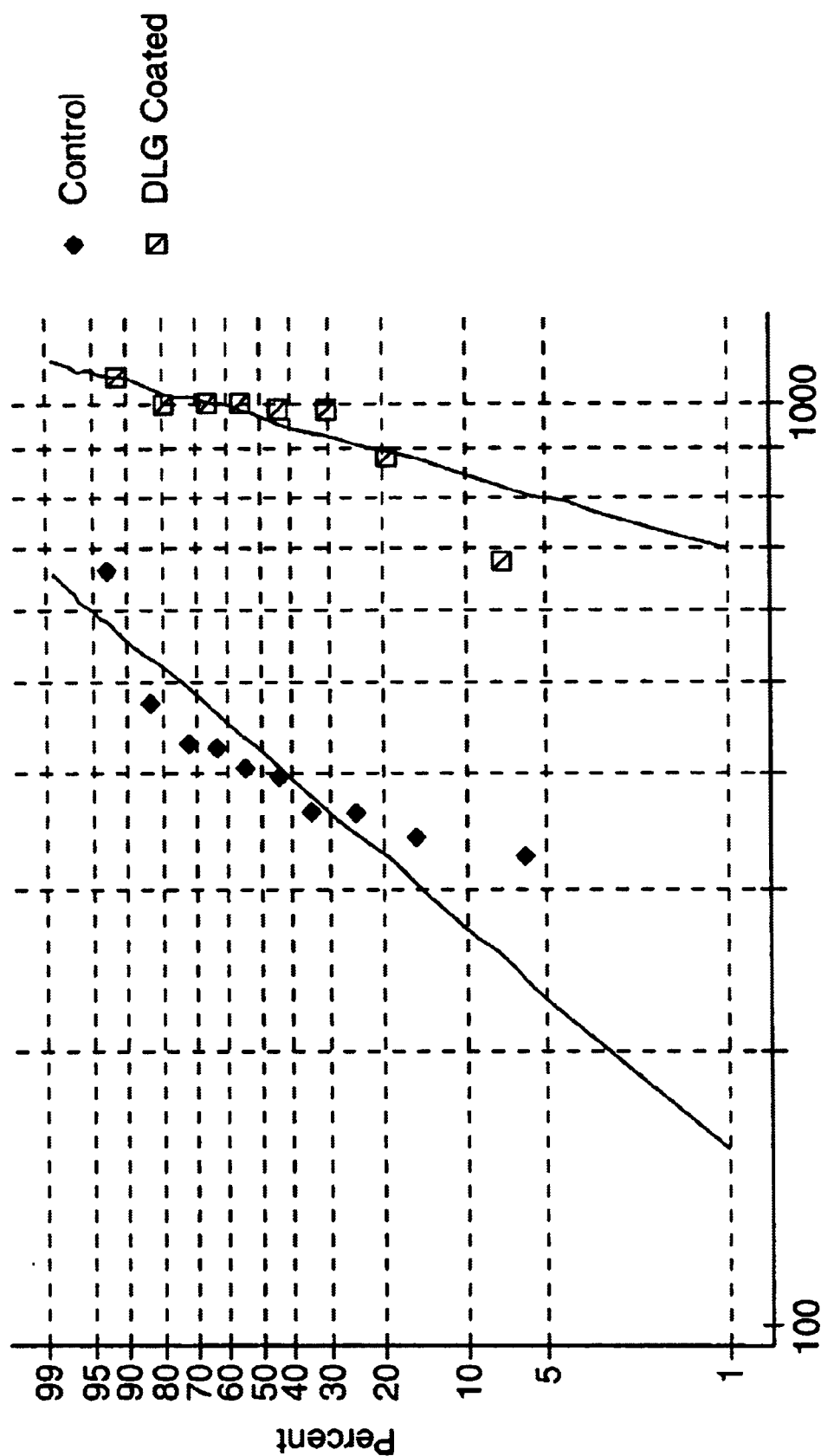
FIG. 6 is a Weibull plot of glass capillaries including a diamond-like glass thin film further described in Example 5. A description of a Weibull plot may be found in 3M Technical Publication: Frederick Bacon, "Silica Optical Fibers—Application Note" available from 3M Optical Transport Systems, Connecticut.

This example demonstrate the application of a diamond-like film disposed on at least a portion of the substrate which imparts low fluoresence and mechanical strength properties of DLG thin films on glass capillaries. Experimental glass capillaries composed of pure silica glass, drawn from a silica tube, to a capillary with an OD of 200 microns and ID of 50 microns. As part of the draw process, this silica capillary is coated with an acrylated urethane (available from DSM Desotech Inc., Elgin, Ill.) to a diameter of 300 microns. The acrylate coating was acid stripped by dipping a 19-cm section of capillary sequentially into fuming sulfuric acid (185° C.) and water that were poured into two separate beakers. The section of capillary was in each liquid for about 30 seconds. The sectionally stripped glass capillaries were mounted to a sample holder with the stripped section located in free-span and thus not making mechanical contact to any other surface. The sample holder was mounted against the powered electrode of Plasma Reactor One described above. The surface of the capillary facing away from the electrode was pre-cleaned using oxygen plasma at 13.3 Pa (100 mTorr) and 400 Watts for 15 seconds. After cleaning the first side, the chamber was opened, the holder was flipped around, the chamber was closed and the other side of the capillary was similarly pre-cleaned. After oxygen plasma cleaning, DLG films were deposited on the surfaces of the fibers by exposing each side of the fiber to a second plasma for 10 minutes. The second plasma was formed from a mixture of tetramethylsilane (TMS) and oxygen. The flow rate of TMS and oxygen were 150 standard cubic centimeters (sccm) and 100 sccm, respectively. The pressure and RF power were maintained at 40 Pa (300 mTorr) and 200 Watts respectively. The RF power was pulsed at a duty cycle of 90% duty cycle at 10 Hz pulsing frequency. DLG films were deposited for five minutes on each side of the. Mechanical strength of the capillaries was tested using a Vytran proof tester (Model PTR-100, available from Vytran Corporation, Morganville, N.J.). In order to simulate mechanical handling, the acid stripped section was wiped once with fingers. The capillaries were mounted in the Vytran Tester and the ultimate strength recorded. In the case where the maximum load was inadequate to break the capillaries, the maximum load was recorded and the actual strength of the capillaries is higher than the recorded value. The mechanical strength results are summarized in FIG. 6. Without any coating, the glass capillaries are prone to fracture whereas, excepting for one sample (strength may have dropped due to a special cause such as contact with the beaker during acid stripping), all the capillary samples failed to break at the testing limit of the proof tester.

The efficacy of the DLG encapsulated glass capillary for capillary electrophoresis is demonstrated by the lack of fluoresence when imaged in a fluoresence microscope. The coating was confirmed to be nominally 2 microns thick based on growth rate measurements made on glass slides with a stylus profilometer: Tencor Instruments, Model No. AS500, Mountainview, Calif. A dramatic difference in the intensity of fluoresence may be seen, with the DLG encapsulated fiber displaying little if any fluoresence.

Figure 7:
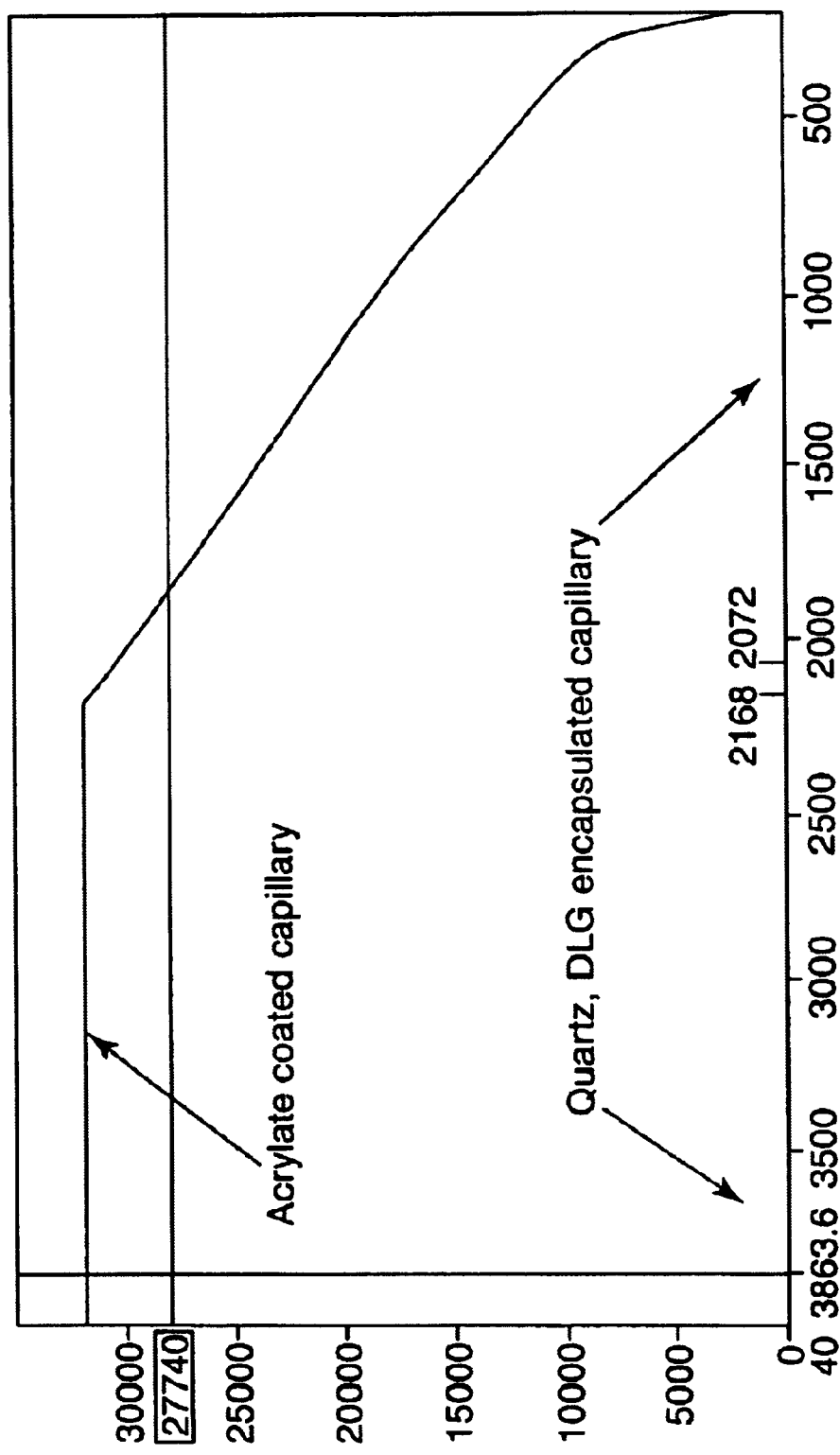
FIG. 7 depicts Raman spectra of the fluorescence measurements referenced in FIG. 1.

The benefits of the DLG encapsulated capillaries were further quantified by making fluoresence measurements with a Raman spectrometer. The samples were further analyzed using the Renishaw system 1000 (Renishaw Instruments, Model 1000, Gluocestershire, UK). The laser excitation was with an Argon Ion laser operating at 488 nm. The 20X objective was used and a single scan was taken on each sample. In addition to the DLG encapsulated capillaries, bare quartz substrate and acrylate encapsulated capillaries were also evaluated for comparison and the results are summarized in FIG. 7. This measurement demonstrates that above 3000 cm$^{-1}$, the magnitude of fluoresence is less than 200 counts for both DLG enacapsulated and bare quartz whereas it is higher than 30000 counts for the acrylate coated capillary.

The results of this example demonstrate a glass capillary with good mechanical strength durability with little or no fluoresence.

Example 2

This example illustrates the utility of a hydrophilic DLG film in a microfluidic device involving microchanneled polymer plates. Applications of microfluidic devices include the transport of biological fluids, heat transfer fluids, low-friction/drag surfaces, etc. In this example, the substrate was an experimental polymethylmethacrylate (PMMA) plate having microchannels for transporting liquids including water. The microchanneled polymer plate was prepared by molding poly(methylmethacrylate) sheet (Plexiglass™ DR101 from Rohm and Haas Co of Philadelphia, Pa.) against a nickel molding tool containing ribs and reservoirs that correspond to the channel and reservoirs in the polymer plate. The tool measured 26.5 cm by 26.5 cm. The sheet of DR 101 (nominally 250 µm thick) and molding tool were brought into contact with each other at a temperature of 187° C. at a pressure of 6.3×10$^5$ Pascal for 2 minutes, after which the pressure was increased to 3.2×10$^6$ Pascal for 2.5 minutes. Thereafter the temperature was decreased to nominally 50° C., and the mold and sheet were then separated.

Using Plasma Reactor Number Two described above, the microchanneled PMMA plate surface was primed initially with an oxygen plasma for 60 seconds at a pressure and RF power of 50 mTorr and 500 Watts, respectively. The flow rates of TMS and oxygen for Sample A were 24 sccm (standard cubic centimeters per minute) and 750 sccm, respectively. One side of the PMMA surface having the channels was treated for five minutes resulting in a DLG thin film thickness of 600 nanometers determined with a Tencor Instruments stylus profilometer. The surface layer of Sample A was further processed to convert the DLG surface to a hydrophilic surface by exposing it to an oxygen plasma at a power and pressure of about 50 mTorr and about 500 Watts, respectively, for 2 minutes. The surface was completely wettable to water, with a contact angle of less than 10 degrees.

Example 3

This example illustrates the moisture barrier properties of DLG films imparted to polymeric capillaries.

A capillary with O.D. of about 360 microns and I.D. of 50 microns was prepared from the polymer Zeonex 480R (Zeon Chemicals L.P.,4100 Bells Lane, Louisville, Ky. 40211, U.S.A.) in the homebuilt plasma reactor (Reactor No.1). The outer surfaces of the capillaries was primed with and oxygen plasma for 2 minutes on each side at a pressure and RF of 100 mTorr and 400 Watts, respectively. The flow rates of TMS and oxygen were 150 sccm and 100 sccm. respectively, resulting in a ratio of TMS to oxygen of 1.5. The pressure and power maintained at 40 Pa (300 mTorr) and 200 Watts respectively. The plasma was operated in a pulsed mode, the pulsing frequency and duty cycle were maintained at 10 Hz and 90%, respectively. Each side of the capillary was exposed to the plasma for five minutes, resulting in a DLG thin film thickness of about 3 microns. The resulting DLG films were optically clear and did not crack or delaminate when the capillaries were bent and flexed.

The DLG thin film prevented the evaporation of water that was stored in the capillary. A 50 cm piece of the treated and untreated capillary were presoaked with water by pumping water through them with a syringe pump for at least one day. They were then filled with a solution of 10 µg/mL of fluorescein in a 20 mM AMPSO, 3-[(1,1-dimethyl-2-hydroxyethyl)amino]-2-hydroxypropanesulfonic acid, C.A.S. registry number 68399-79-1, Sigma Chemical Co., St. Louis, Mo. 63178 buffer at pH 9.0 and then sealed at both ends with an epoxy glue (No. 04001, Elementis Performance Polymers, Bellevue, N.J. 07109). The evaporation of water could then be observed by monitoring the shrinkage of the volume of liquid inside the capillary using a fluorescent microscope. It was observed that the liquid in the untreated capillary shrunk by evaporation through the capillary wall at a rate almost 30 times that of the treated capillary (with a DLG film thereon).

Without the DLG film, the water evaporates by transport through the walls of the capillary. This result demonstrates the excellent barrier properties of the DLG thin film.

The complete disclosures of the patents, patent documents, and publications cited herein arm incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A fluid handling device comprising a substrate and an optically transmissive diamond-like film disposed on at least a portion of the substrate, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen.

2. The fluid handling device of claim 1 comprising a capillary having an internal surface and an external surface, wherein at least a portion of at least one of the internal or external surfaces includes an optically transmissive diamond-like film disposed thereon.

3. The fluid handling device of claim 2 wherein the external surface of the capillary includes an optically transmissive diamond-like film disposed on at least a portion thereof.

4. The fluid handling device of claim 1 comprising a microfluidic article comprising a microfluidic handling architecture comprising a fluid handling surface, wherein at least a portion of the fluid handling surface includes an optically transmissive diamond-like film disposed thereon.

5. The fluid handling device of claim 4 wherein the optically transmissive diamond-like film is also hydrophilic.

6. The fluid handling device of claim 4 comprising:
   a first non-elastic, polymeric substrate comprising a first major surface that includes the microfluidic handling architecture and a second major surface; and
   a second polymeric substrate that is integrally bonded to said second major surface of said fist substrate, wherein the second substrate is capable of forming a free-standing substrate in the absence of said first substrate.

7. The fluid handling device of claim 4 comprising a cover layer on the microfluidic handling architecture.

8. The fluid handling device of claim 7 wherein the cover layer is bonded to the first major surface of the first substrate.

9. The fluid handling device of claim 4 wherein the microfluidic handling architecture comprises selected from the group consisting of microchannels, fluid reservoirs, sample handling regions, and combinations thereof.

10. The fluid handling device of claim 9 wherein at least one of the structures comprises a fluid handling surface, at least a portion of which has the optically transmissive diamond-like film disposed thereon.

11. The fluid device of claim 4 comprising a first polymeric substrate comprising a first major surface that includes a plurality of microfluidic handling architectures and a second major surface, wherein the article is in the form of a roll.

12. The fluid handling device of claim 1 wherein the optically transmissive diamond-like film has disposed thereon linking agents and a reactant affixed to the linking agents to form a binding site.

13. The fluid handling device of claim 12 wherein the linking agents are covalently attached to the diamond-like film.

14. The fluid handling device of claim 12 wherein the reactant is selected from the group consisting of nucleic acids, proteins, and carbohydrates.

15. The fluid handling device of claim 1 wherein the diamond-like film is also hydrophilic.

16. A fluid handling device comprising a microfluidic article comprising a microfluidic handling architecture comprising a fluid handling surface wherein at least portion of the fluid handling surface includes a hydrophilic diamond-like film disposed thereon, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen.

17. A fluid handling device comprising a substrate and an optically transmissive and hydrophilic film disposed on at least a portion of the substrate, wherein the film comprises diamond-like glass comprising a dense random covalent system comprising on a hydrogen-free basis at least about 30 atomic percent carbon, at least about 25 atomic percent silicon, and less than or equal to about 45 atomic oxygen, and further wherein the film has an extinction coefficient of no greater than 0.010 at 250 nm.

18. A fluid handling device comprising a substrate and a diamond-like glass film comprising a dense random covalent system comprising at least about 30 atomic percent carbon, at least about 25 atomic percent silicon, and less than or equal to about 45 atomic percent oxygen, on a hydrogen-free basis, disposed on at least a portion of the substrate.

19. The fluid handling device of claim 18 comprising a capillary having an internal surface and an external surface, wherein at least a portion of at least one of the internal or external surfaces has the film disposed thereon.

20. The fluid handling device of claim 19 wherein at least a portion of the external surface of the capillary has the film disposed thereon.

21. The fluid handling device of claim 18 comprising a microfluidic article comprising a microfluidic handling architecture including a fluid handling surface wherein at least a portion of the fluid handling surface has the film disposed thereon.

22. A fluid handling device comprising a microfluidic article comprising microfluidic handling architecture including a fluid handling surface wherein at least a portion thereof has disposed thereon a film comprising diamond-like glass which comprises a dense random covalent system comprising on a hydrogen-free basis at least about 30 atomic percent carbon, at least about 25 atomic percent silicon, and less than or equal to about 45 atomic percent oxygen.

23. A fluid handing device comprising a microfluidic article comprising a microfluidic handling architecture including a non-fluid handling surface wherein at least a portion thereof has disposed thereon a diamond-like film that is optically transmissive, hydrophilic, or both, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen.

24. A method of manufacturing a fluid handling device comprising a microfluidic article comprising a microfluidic handling architecture comprising a fluid handling surface wherein at least a portion of the fluid handling surface includes a hydrophilic diamond-like film disposed thereon, the method comprising manufacturing a hydrophilic diamond-like film by a method comprising treating a diamond-like film in an oxygen-containing plasma, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen.

25. A fluid handling device comprising a substrate and an optically transmissive diamond-like film disposed on at least a portion of the substrate, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen and further wherein the film exhibits substantially no fluorescence.

26. A fluid handling device comprising a microfluidic article comprising a microfluidic handling architecture comprising a fluid handling surface wherein at least a portion of the fluid handling surface includes a hydrophilic diamond-like film disposed thereon, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen, and further wherein the film exhibits substantially no fluorescence.

27. A fluid handling device comprising a substrate and an optically transmissive diamond-like film disposed on at least a portion of the substrate, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen, and further wherein the film is at least 50 percent transmissive to radiation at one or more wavelengths from about 180 to about 800 nanometers.

28. A fluid handling device comprising a microfluidic article comprising a microfluidic handling architecture comprising a fluid handling surface wherein at least a portion of the fluid handling surface includes a hydrophilic diamond-like film disposed thereon, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen, and further wherein the film is at least 50 percent transmissive to radiation at one or more wavelengths from about 180 to about 800 nanometers.

29. A method of manufacturing a fluid handling device comprising a microfluidic article comprising a microfluidic handling architecture comprising a fluid handling surface wherein at least a portion of the fluid handling surface includes a hydrophilic diamond-like film disposed thereon, the method comprising manufacturing a hydrophilic diamond-like film by a method comprising treating a diamond-like film in an oxygen-containing plasma, wherein the film comprises diamond-like glass comprising a dense random covalent comprising on a hydrogen-free basis at least about 30 atomic percent carbon, at least about 25 atomic percent silicon, and less than or equal to about 45 atomic percent oxygen, and further wherein the film exhibits substantially no fluorescence.

30. A method of manufacturing a fluid handling device comprising a microfluidic article comprising a microfluidic handling architecture comprising a fluid handling surface wherein at least a portion of the fluid handling surface includes a hydrophilic diamond-like film disposed thereon, the method comprising manufacturing a hydrophilic diamond-like film by a method comprising a diamond-like film in an oxygen-containing plasma, wherein the film comprises diamond-like glass comprising a dense random covalent system comprising on a hydrogen-free basis at least about 30 atomic percent carbon, at least about 25 atomic percent silicon, and less than or equal to about 45 atomic percent oxygen, and further wherein the film is at least 50 percent transmissive to radiation at one or more wavelengths from about 180 to about 800 nanometers.

* * * * *

UNITED STATES PATENT AND TRADEMARK OFFICE
CERTIFICATE OF CORRECTION

PATENT NO.    : 6,749,813 B1
DATED         : June 15, 2004
INVENTOR(S)   : David, Moses M.

It is certified that error appears in the above-identified patent and that said Letters Patent is hereby corrected as shown below:

Column 2,
Line 34, delete "fast" and insert -- first --, therefor.
Line 65, after "plasma" insert -- . --.

Column 6,
Line 29, after "and" delete "U.S. Pat. Nos.".

Column 7,
Line 38, delete ";" and insert -- , --, therefor.

Column 8,
Line 3, delete ";" and insert -- , --, therefor.
Line 28, after "of" delete "in".
Line 37, delete "immnunoassay" and insert -- immunoassay --, therefor.
Line 52, delete "09/519,444" and insert -- 09/519,447 --, therefor.

Column 10,
Lines 21-22, delete ""Gram to atom"" and insert -- "Gram atom" --, therefor.

Column 12,
Line 65, after "methane," delete "to".

Column 13,
Line 11, after "chamber" insert -- will cause the source to volatilize. Alternatively, the additional components may be entrained in an inert gas stream. The additional components may be --.
Line 35, delete "asymmetnc" and insert -- asymmetric --, therefor. --.

Column 15,
Line 31, after "of" delete "to".
Line 32, after "plasma" insert -- . --.

Column 18,
Line 20, delete "arm" and insert -- are --, therefor.
Line 61, delete "fist" and insert -- first --, therefor.

UNITED STATES PATENT AND TRADEMARK OFFICE
CERTIFICATE OF CORRECTION

PATENT NO. : 6,749,813 B1
DATED : June 15, 2004
INVENTOR(S) : David, Moses M.

It is certified that error appears in the above-identified patent and that said Letters Patent is hereby corrected as shown below:

Column 19,
Line 2, after "comprises" insert -- structures --.
Line 9, after "fluid" insert -- handling --.
Line 28, after "least" insert -- a --.
Line 42, after "atomic" insert -- percent --.
Line 64, after "comprising" insert -- a --.

Column 20,
Line 33, after "oxygen" insert -- , --.

Signed and Sealed this

Sixteenth Day of November, 2004

JON W. DUDAS
*Director of the United States Patent and Trademark Office*